United States Patent [19]

Lorenz et al.

[11] Patent Number: 4,659,359

[45] Date of Patent: Apr. 21, 1987

[54] 2-CHLORO-4,6-DIAMINO-S-TRIAZINES AS ALGICIDES

[75] Inventors: Joachim Lorenz; Reinhardt Grade, both of Bensheim, Fed. Rep. of Germany

[73] Assignee: Ciba-Geigy Corporation, Ardsley, N.Y.

[21] Appl. No.: 814,520

[22] Filed: Dec. 19, 1985

Related U.S. Application Data

[63] Continuation of Ser. No. 638,548, Aug. 7, 1984, abandoned, which is a continuation of Ser. No. 556,076, Dec. 1, 1983, abandoned, which is a continuation of Ser. No. 376,339, May 10, 1982, abandoned, which is a continuation of Ser. No. 214,297, Dec. 8, 1980, abandoned.

[30] Foreign Application Priority Data

Dec. 18, 1979 [CH] Switzerland .............. 11213/79

[51] Int. Cl.$^4$ .............. A01N 59/00; A01N 43/70
[52] U.S. Cl. ................... 71/67; 71/82; 210/764; 514/245
[58] Field of Search ............ 210/764; 71/65, 67, 71/82, 93; 514/245

[56] References Cited

U.S. PATENT DOCUMENTS

| | | | |
|---|---|---|---|
| 3,136,716 | 6/1964 | Kitter | 71/67 |
| 3,161,588 | 12/1964 | Zsoldos, Jr. | 71/67 |
| 3,201,311 | 8/1965 | Antonides et al. | 71/67 |
| 3,253,979 | 5/1966 | Robson | 71/67 |
| 3,459,751 | 8/1969 | Nikles | 71/93 |

FOREIGN PATENT DOCUMENTS

| | | | |
|---|---|---|---|
| 1140396 | 11/1962 | Fed. Rep. of Germany | 71/93 |
| 0025135 | 3/1974 | Japan | 71/67 |
| 1336049 | 11/1973 | United Kingdom | 71/93 |

OTHER PUBLICATIONS

Skarka et al., "Antialgal Properties, etc.," (1977), CA 88:46185; (1978).
Ordog, "Effect of Triazine Herbicides, etc.," (1979), CA 91:205,565p (1979).
Wilson et al., "Antialgal Substances, etc.," (1977), CA 88:126128h (1978).
Anon, "3-Isothiazolone/Halogen, etc.," (1977), CA 88:17124n (1978).

Primary Examiner—Glennon H. Hollrah
Assistant Examiner—Robert Lelkesi
Attorney, Agent, or Firm—Harry Falber

[57] ABSTRACT

Mixtures of
(a) a 2-chloro-4,6-diamino-s-triazine of the formula I

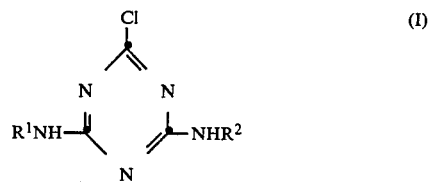

wherein $R^1$ is alkyl having 2-5 C atoms or cycloalkyl having 3-5 C atoms, and $R^2$ is alkyl having 3-5 C atoms or cycloalkyl having 3-5 C atoms, and
(b) active halogen or an agent releasing active halogen are suitable for the combating of algae and simultaneous disinfection in water reservoirs, particularly in swimming-baths, and also in cooling-water circulation systems.

1 Claim, No Drawings

2-CHLORO-4,6-DIAMINO-S-TRIAZINES AS ALGICIDES

This application is a continuation of application Ser. No. 638,548, filed Aug. 7, 1984, now abandoned, which is a continuation of application Ser. No. 556,076, filed Dec. 1, 1983, now abandoned, which is a continuation of application Ser. No. 376,339, filed May 10, 1982, now abandoned, which is a continuation of application Ser. No. 214,297, filed Dec. 8, 1980, now abandoned.

The invention relates to the use of specific 2-chloro-4,6-diamino-s-triazines in combination with active halogen, particularly chlorine, for combating algae in water reservoirs, especially in swimming-baths, and also in cooling-water circulation systems.

The water in a swimming-bath can be maintained fresh by the continuous supply of fresh water and the discharge of used water, a process which results in a high consumption of fresh water. Swimming-baths are usually only rarely refilled with fresh water, and attempts are made to keep the amount of water contained as long as possible clean and free from germs and algae. This is achieved in most cases by means of filtration of the circulating water and by the addition of germicidal (bactericidal) and algicidal chemicals. This applies to open-air baths and to indoor swimming-baths, as well as to other water reservoirs and to cooling-water circulation systems.

Mainly hypochlorites or other substances releasing "active halogen" are used for the bactericidal treatment, and ozone too is used to a certain extent. Algicides hitherto employed have been especially quaternary ammonium compounds as well as copper or silver compounds, and more recently also triazine derivatives, which were known as herbicides, for example 2-alkylthio-4,6-diamino-s-triazines, have been suggested for this purpose.

Quaternary ammonium compounds have the disadvantages of tending to froth, of raising the pH value, of exhibiting only slight activity against blue algae, and of having an effect which rapidly subsides. Copper and silver compounds have the disadvantage that they discolour the water and are not effective against green algae, and that likewise their action quickly diminishes.

The triazine derivatives mentioned do not have these disadvantages. The 2-alkylthio-4,6-diamino-s-triazines (for example ametryne, prometryne or terbutryne) have so high an activity that they are successfully used for example fo combating algae in natural lakes. They cannot however be used in chlorinated water tanks, since the compounds are not stable to chlorine.

It has already been suggested that 2-alkylthio-4,6-diamino-s-triazines be used in combination with the more weakly oxidising iodine as disinfectants, which would however give rise to considerably higher costs, and the method has not therefore been used in practice (E. L. Nilson, R. F. Unz. Appl. and Environmental Microbiology, Dec., 1977, pp. 815–822).

There has been therefore suggested, for combating algae in chlorine-containing water tanks, simazine, (2-chloro-4,6-bis-(ethylamino)-s-triazine), which is largely stable to chlorine. The algicidal activity of simazin is of course considerably less than that of the alkylthiotriazines mentioned above. A consequence of this lesser activity is that simazin has to be used at a concentration which renders it harmful to plants of a higher order. This manifests itself disadvantageouly when for example the cultivated plants surrounding a swimming-pool are impaired by spray from the pool.

The object of the invention was to find triazine derivatives which are not sensitive to halogens, and which have an action against algae that is so much greater than their action against plants of a higher order that it is possible, within a concentration range sufficient wide for practical purposes, to completely prevent the growth of algae, without any risk to plants of a higher order.

It has been found that specific 2-chloro-4,6-diamino-s-triazines exhibit a sharply graduated activity against algae on the one hand and plants of a higher order on the other hand, and that this graduation can be heightened in a synergistic manner by combination of these triazines with halogen, especially with chlorine or with substances releasing chlorine.

The invention relates therefore to the use of a mixture of (a) a 2-chloro-4,6-diamino-s-triazine of the formula I

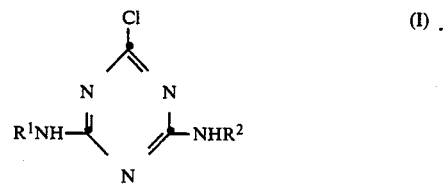

wherein $R^1$ is alkyl having 2–5C atoms or cycloalkyl having 3–5C atoms, and $R^2$ is alkyl having 3–5C atoms or cycloalkyl having 3–5C atoms, and (b) active halogen, or an agent releasing active halogen, for the combating of algae and simultaneous disinfection in water tanks, especially in swimming-baths, and also in cooling-water circulation systems.

The radical $R^1$ can be a straight-chain or branched-chain alkyl group, for example ethyl, propyl, isopropyl, n-butyl, isobutyl, sec-butyl, tert-butyl or isoamyl. As alkyl, $R^2$ can likewise be straight-chain or branched-chain, for example propyl, isopropyl, n-butyl, isobutyl, sec-butyl, tert-butyl or isoamyl. As cycloalkyl, $R^1$ and $R^2$ can be cyclobutyl or cyclopentyl, particularly however cyclopropyl.

The triazines of the formula I usable according to the invention are known compounds, and in part are used commercially as herbicides. The use of 2-chloro-4-ethylamino-6-tert-butyl-s-triazine, also known under the abbreviated name of terbutylazine, in combination with active chlorine is preferred.

The main field of application of the invention is swimming-baths; it can however be extended to other containers of water, for example rain-water-collecting tanks, fire-extinguishing pools or storage tanks for non-drinkable water. The algae occurring in water containers of this kind are in particular blue-green algae (black algae), which include for example Oscillatoria and Phormidium, and which grow especially on the walls of the containers, and also green algae, such as Chlorella and Scenedesmus, which are free-floating and cause the green colour of the water.

A further field of application for the mixtures according to the invention is cooling-water circulation systems, for example in power stations, chemical production plants, heat pumps or air-conditioning plants. A growth of algae in such installations impairs the heat transfer and hence the effectiveness of the circulation system.

Preferably used as component (b) of the mixture used according to the invention is active chlorine or an agent releasing chlorine. Substances releasing active halogen are for example hypochlorites, such as the solutions which are sold as "chlorine bleach liquors" and which contain mainly sodium hypochlorite; as well as chloride of lime, chloroamines, trichloroisocyanuric acid, dichloroisocyanuric acid, and sodium salts thereof, dichlorodimethyl hydantoin, chlorobromodimethyl hydantoin and dibromodimethyl hydantoin. The practice in the case of fairly large water containers or tanks is also to feed in directly chlorine gas or bromochloride. The content of "active halogen" can be measured by iodometric titration of the treated water.

The amount of triazine compounds of the formula I, in combination with active chlorine, required to prevent the growth of algae is about 0.1 to 1 mg/l, and the concentration of "active chlorine" should be about 0.05 to 3 mg/l. This is an amount of chlorine which is in any case customarily required for the disinfection of swimming-baths. The synergistic effect can therefore be obtained without any increase in the usual amount of chlorine. In cooling-water circulation systems, a higher amount of chlorine may be needed in the case where chlorine-consuming impurities are present, particularly with a discontinuous form of treatment. These low concentrations of triazine derivatives in combination with chlorine are to a great extent harmless to plants of a higher order, whereas with the use of the hitherto known 2-chloro-4,6-diaminotriazines, for example simazin, it is necessary, even when used in combination with chlorine, to use such a high concentration that adjacent ornamental plants can be harmed by spray.

The Examples which follow illustrate these differences by means of tests with various algae cultures.

EXAMPLE 1

Determination of the minimum inhibitory concentration (MIC) against algae in the Agar incorporation test.

The cultures of the various algae strains, grown in an algae nutrient medium over a period of 14 days:

Oscillatoria geminata,
Nostoc spec.,
Phormidium foveolarum,
Anacystis nidulans,
Chlorella vulgaris,
Chlorella pyrenoidosa,
Scenedesmus spec.,
Ulothrix subtilissima and
Tribonema aequale were diluted in the algae nutrient medium 1/100 and 1/200, respectively. The suspensions were applied dropwise to algae agar, which contained the biocide at three different concentrations. After an incubation time of 14 days at room temperature, with a daily cycle of 14 hours of light and 10 hours of darkness, the growth occurring was assessed. The results are summarised in Table 1.

TABLE 1

| MIC determination (examined active-substance concentration 3, 10 and 30 mgl) in the Agar-incorporation test | | | | | | |
|---|---|---|---|---|---|---|
| Strains | A | B | C | D | E | F |
| Oscillatoria geminate | 3 | 30 | 3 | 3 | 3 | 10 |
| Nostoc spec. | 10 | 10 | 3 | 3 | 3 | 3 |
| Phormidium foveolarum | 30 | 3 | 3 | 3 | 3 | 3 |

TABLE 1-continued

| MIC determination (examined active-substance concentration 3, 10 and 30 mgl) in the Agar-incorporation test | | | | | | |
|---|---|---|---|---|---|---|
| Strains | A | B | C | D | E | F |
| Anacystis nidulans | 3 | 30 | 3 | 3 | 3 | 3 |
| Chlorella vulgaris | 3 | 3 | >30 | 3 | 3 | 10 |
| Chlorella pyrenoidosa | 10 | 3 | >30 | 3 | 3 | 10 |
| Scenedemus spec. | 3 | 3 | 3 | 3 | 3 | 3 |
| Ulothrix subtilissima | 3 | 3 | 3 | 3 | 3 | 3 |
| Tribonema aequale | 3 | 3 | 3 | 3 | 3 | 3 |

A = $Cu_2O$
B = quaternary ammonium mixture
C = simazin (2-chloro-4,6-bis-(ethylamino)-s-triazole
D = tertbutylazine (2-chloro-4-ethylamino-6-t-butyl-amino-s-triazine)
E = 2-chloro-4-cyclopropylamino-6-t-butylamino-s-triazine
F = 2-chloro-4-cyclopropylamino-6-sec-butylamino-s-triazine As can be seen from Table 1, the copper compounds have only a weak action against blue algae. Simazin is not effective against Chlorella strains. The compounds D and E on the other hand have a broad spectrum of action against all the algae strains examined in this test.

EXAMPLE 2

Determination of the minimum inhibitory concentration (MIC) against algae in a liquid culture The cultures of the following algae strains, grown in an algae nutrient medium over a period of 14 days:

Oscillatoria geminata,
Nostoc spec.,
Phromidium fovoelarum,
Anacystis nidulans,
Chlorella vulgaris,
Chlorella pyrenoidosa,
Scenedesmus spec.
Ulothrix subtilissima, and
Tribonema aequale were diluted, in a vessel for producing a mixed culture, in an algae nutrient medium 1/100 and 1/200. The algicides were added all at once to the respective suspensions. The bleaching liquor was added immediately and in each case after one week of incubation in a shaking machine at 18° C. with a daily cycle of 14 hours of light and 10 hours of darkness. The test was assessed by visual observation after 4, 6 and 8 weeks. Also photographs were taken after 8 weeks' incubation. The results are summarised in Table 2.

TABLE 2

| MIC determination in a liquid culture against a mixed culture of algae | | | | | |
|---|---|---|---|---|---|
| Single dosage | | Weekly dosage | | | |
| Algicide according to Example 1 | Conc. (mg/l) | bleaching liquor conc. (mg active chorine/l) | Growth | | |
| | | | 4 | 6 | 8 weeks |
| C | 0,5 | — | + | + | + |
| | 1 | — | + | + | + |
| | 3 | — | (−) | (+) | + |
| | 30 | — | (−) | (+) | + |
| D | 0,5 | — | (+) | + | + |
| | 1 | — | (−) | (+) | + |
| | 3 | — | — | — | — |
| E | 0,5 | — | (+) | (+) | + |
| | 1 | — | (+) | (−) | (+) |
| | 3 | — | — | — | — |
| F | 0,5 | — | + | + | + |
| | 1 | — | (+) | + | + |
| | 3 | — | (−) | (−) | (+) |
| — | — | 0,1 | + | + | + |
| — | — | 0,2 | + | + | + |
| — | — | 0,3 | (−) | (+) | + |
| — | — | 0,5 | (−) | (+) | + |
| D | 0,5 | 0,3 | — | — | — |

TABLE 2-continued

| MIC determination in a liquid culture against a mixed culture of algae | | | | | |
|---|---|---|---|---|---|
| Single dosage | | Weekly dosage | | | |
| Algicide according to Example 1 | Conc. (mg/l) | bleaching liquor conc. (mg active chorine/l) | Growth 4 | 6 | 8 weeks |
| C | 0,5 | 0,3 | + | + | + |
| F | 0,5 | 0,3 | (−) | (+) | + |
| E | 0,5 | 0,3 | (−) | (−) | (+) |
| D | 1 | 0,3 | − | − | − |
| C | 1 | 0,3 | (−) | (+) | + |
| F | 1 | 0,3 | (−) | − | − |
| E | 1 | 0,3 | (−) | (−) | (−) |
| control | — | — | + | + | + |

+ = growth as control,
(+) = growth less than control
(−) = scarcely perceptible growth,
− = no growth It is seen from Table 2 that in order to prevent growth of the mixed culture, 3 ppm of active substance are required with a single dosage of D or E on its own, whereas the amount required of active chlorine on its own to achieve the same effect is more than 0.5 ppm weekly. The algicides C and F alone have no growth-inhibiting action against the mixed culture examined. A synergistic effect surprisingly occurs with use of a combination of D or E or F with bleaching liquor. A single dosage of 0.5 ppm of D or 1 ppm of E or 1 ppm of F jointly with a weekly dosage of 0.3 ppm of active chlorine is sufficient to prevent the growth of algae over a period of 8 weeks.

With a combination of simazin and active chlorine, more than 1 ppm and simazin is required to eventually prevent growth of algae. A concentration of more than 1 ppm of simazin is however harmful to the plants of a higher order growing adjacent to the swimming-bath.

EXAMPLE 3

Treatment of a swimming-bath

A 55 m³ private swimming-bath was treated over a period of 4 months in summer with terbutylazine and Trichloroisocyanuric acid, NaOCl or CaOCl. The swimming-bath was provided with a sand-filter plant having a circulation capacity of 40 m³/hour. The filter plant was switched on for about 6 hours per day. The water had a hardness of 24° dH, and the pH adjustment to pH=7.2 was effected each time with NaHSO₄. The chlorine addition (firstly in particular trichloroisocyanuric acid and then more NaOCl or CaOCl) was made every 8–14 days in order to keep an active-chlorine content of >1.2<2 ppm of Cl₂. The 50% aqueous formulation of terbutylazine was added every 2–5 weeks to maintain a terbutylazine concentration (determined by thin-layer chromatography) of >0.5≦1 ppm. In spite of full exposure to sunlight over the whole period of 4 months, there was no growth of bacteria and algae in the clear water; furthermore, there was no frothing at all of the water or damage to the plants surrounding the swimming-bath.

EXAMPLE 4

Action in a model circulation system

The model circulating systems located on the roof of a three-storied house each consisted of:
(a) a plastics vat having a volume of 120 liters,
(b) a Siemens pump (21 l/min. with a 3 m lift), and
(c) a cooling tower containing pine, larch, oak, spruce, asbestos-cement and PVC plates.

Evaporated water (about 10–20 l/24 h) was continuously replaced by fresh water (5–7 l/h). There occurred a natural inoculation by the falling in of dust and pollen (direct solar irradiation).

The three model circulating systems were treated with:

1. 3 ppm of a.i. Cl₂Na-dichloroisocyanuric acid twice weekly,
2. 3 ppm of a.i. terbutylazine (50% aqueous formulation) twice weekly,
3. 3 ppm of a.i. Cl₂Na-dichloroisocyanuric acid twice weekly+2 ppm of a.i. terbutylazine (50% aqueous formulation) twice weekly.

(a.i.=active ingredient).

2 ppm of a.i. terbutylazine were added portionwise because, with a half-life period of about 20 hours in the system by virtue of about 5–7 l/h of fresh water, the concentration of active substance as a result of this intermittent treatment fell to 0.1–0.2 ppm. A decrease to below this value of 0.1–0.2 ppm should be avoided if the treatment is to be successful.

The model circulating system treated with Na-dichloroisocyanuric acid exhibited growth of algae mucilage on the various woods after about 4 weeks, the model treated with terbutylazine after about the same time, and the untreated model after one week.

The circulating system treated with the combination of Na-dichloroisocyanuric acid and terbutylazine exhibited however even after 90 days of treatment no signs whatsoever of the formation of algae or bacterial mucilage.

What is claimed is:

1. In the method of inhibiting the growth of algae in aqueous media susceptible to algae growth by the addition of active chlorine from an alkali or alkaline earth metal hypochlorite source and a 2-chloro-4,6-diamino-s-triazine, the improvements comprising utilizing (1) 2-chloro-4-ethylamino-6-tert-butylamino-s-triazine and (2) concentration ranges of 0.1 to 0.5 mg/l. of active chlorine and 0.1 to 1.0 mg/l. of s-triazine.

* * * * *